United States Patent [19]
Gallopo

[11] Patent Number: 4,490,269
[45] Date of Patent: Dec. 25, 1984

[54] EFFERVESCENT DENTURE CLEANING COMPOSITION COMPRISING MONOPERPHTHALATE

[75] Inventor: Andrew R. Gallopo, Garfield, N.J.

[73] Assignee: Warner-Lambert Company, Morris Plains, N.J.

[21] Appl. No.: 570,475

[22] Filed: Jan. 13, 1984

[51] Int. Cl.$^3$ .......................... C11D 7/12; C11D 7/38; C11D 7/54
[52] U.S. Cl. ......................................... 252/94; 252/95; 252/99
[58] Field of Search ............................... 252/99, 94, 95

[56] References Cited

U.S. PATENT DOCUMENTS

| | | | |
|---|---|---|---|
| 2,931,776 | 4/1960 | Howard | 252/99 X |
| 3,337,466 | 8/1967 | Puetzer et al. | 252/99 X |
| 3,488,288 | 1/1970 | Hill | 252/95 X |
| 3,494,786 | 2/1970 | Nielsen | 252/95 X |
| 3,494,787 | 2/1970 | Lund et al. | 252/95 X |
| 3,607,759 | 9/1971 | Barth | 252/99 X |
| 4,225,451 | 9/1980 | McCrudden et al. | 252/99 |
| 4,403,994 | 9/1983 | Hignett | 252/94 X |
| 4,405,486 | 9/1983 | Eoga | 252/174 X |

FOREIGN PATENT DOCUMENTS 1052796 12/1966 United Kingdom ................. 252/99

*Primary Examiner*—John E. Kittle
*Assistant Examiner*—Mukund J. Shah
*Attorney, Agent, or Firm*—Gary M. Nath; Charles A. Gaglia

[57] ABSTRACT

A denture cleansing composition comprising an effervescent agent and as a bleaching agent a monoperphthalate or a potassium monopersulfate and a monoperphthalate.

31 Claims, No Drawings

EFFERVESCENT DENTURE CLEANING COMPOSITION COMPRISING MONOPERPHTHALATE

BACKGROUND OF THE INVENTION

Dentures and other removable orthodontic appliances have in the past been cleansed by brushing. In more recent years various cleansing compositions have been developed to permit thorough and convenient cleansing of such orthodontic appliances by soaking in a solution of the cleansing composition. These products have been improved by adding to the formulations, in tablet or granular form, various compounds to cause effervescence in the cleansing solution. This effervescence aids in dispersing the formulation both by generating a "stirring" action and by "exploding" the tablet or granule as a result of internal gas generation within the tablet or granule. See for example, U.S. Pat. No. 2,931,776 which teaches the use of an anhydrous perborate in a denture cleanser to cause effervescence. The sodium perborate releases oxygen which in addition to causing effervescence contributes, to a minor extent, to the bleaching of the orthodontic appliance.

Potassium monopersulfate has been used as a bleaching agent for dentures. U.S. Pat. No. 3,243,377 discloses a composition containing either anhydrous sodium perborate or potassium monopersulfate in conjunction with an organic acid and a cleansing completion indicator.

U.S. Pat. No. 4,405,486 discloses a method for stabilizing the perborate salts by mixing the perborate with a polymeric fluorocarbon, compressing the mixture and then granulating the composition for use in denture cleaning compositions. As used in the specification and claims the term "denture" means all those removable orthodontic appliances such as false teeth, dental plates and bridges.

In an effort to improve the effectiveness of denture cleansing compositions U.S. Pat. No. 3,936,385 discloses the use of a chlorine generating compound such as dichloroisocyanurates. Although these chlorine generating compositions are effective cleansing agents they are not well accepted because of the chlorine odor.

Chlorine free bleaches which rely on the generation of active oxygen have long been known in the art for use in laundry detergents. These compounds use perborates and persulfates as the oxygen containing compounds of the composition.

British Pat. No. 886,188, discloses certain peroxy acids for use in laundry detergents. In particular, substituted perbenzoic acids, such as chloroperoxybenzoic acid are said to have improved stability over other peracids. British Pat. No. 1,269,677, discloses a synergistic bleaching effect when monopersulfates are used in conjunction with organic peroxy acids. Such monopersulfates are believed to consist essentially of the triple salt $KHSO_5$ $KHSO_4$ $K_2SO_4$ $KHSO_4$ $K_2SO_4$ and $2KHSO_5$. In the mole ratio of about 2:1:1 the foregoing triple salt is known commercially as OXONE ® and sold by E. I. duPont De Nemours & Co. Inc.

U.S. Pat. No. 3,773,673 teaches similar laundry detergent compositions wherein the ratio of monopersulfate to organic peroxy compound is about 1:1 to 1:3. A preferred pH range for effective use of the persulfate/peracid combination of 8.5–11 is disclosed. The preferred organic peroxy compounds are the substituted perbenzoic acids, e.g., p-methoxyperbenzoic acid, and their alkali metal or ammonium salts.

The organic peroxy acids, however, are generally unstable and various methods have been used to improve their stability. The aforementioned British Pat. No. 1,269,677 discloses a stabilizing method which consists of blending the organic peroxy acid with inert compounds to minimize the contact between the peroxy acids and other compounds of the composition, the inert compound being removed by solution, melting or abrasion in the washing process. U.S. Pat. No. 4,126,573, discloses peroxy acids coated with surfactants useful in bleaching fabrics.

Other combinations of organic peroxy acids for use in laundry detergents are disclosed in an EPC application published Jan. 6, 1983 under publication number 0 068 547. A combination of a hydrophilic organic peroxy acid and a hydrophobic peroxy acid are disclosed to have improved effectiveness in laundry bleaches. U.S. Pat. No. 4,126,573 discloses peroxy acids coated with surfactants.

U.S. Pat. No. 4,325,828 discloses a laundry bleach composition which comprises an organic peroxy acid in combination with a perborate salt as the bleaching agent.

There have been no disclosures of which this inventor is aware, of the use of organic peroxy acids in denture cleansing compositions. A primary reason is that the most economical and stable organic peroxy acids which have been available are the substituted perbenzoic acids, and these compounds are not sufficiently stable to be used in denture cleansing composition.

SUMMARY OF THE INVENTION

It has surprisingly been found that a stable denture cleansing composition of improved quality can be prepared by using monoperphthalic acid as a component of the bleaching agent of the denture cleansing composition. A perborate or monopersulfate is used in conjunction with a monoperphthalic acid. In a preferred embodiment at least one perborate and at least one monopersulfate are used together in conjunction with the monoperphthalic acid.

The cleansing composition of this invention may be compressed into a tablet or granules which includes in the composition, agents to cause effervescence upon contact with water.

DETAILED DESCRIPTION

This invention relates to a denture cleansing composition which utilizes monoperphthalic acid as the bleaching agent. In particular it relates to effervescent denture cleansing compositions which incorporate perborates and persulfates in the composition to give improved bleaching characteristics.

In its preferred embodiment, the denture cleansing composition of this invention is formulated to effervesce when dissolved in water. Effervescent cleansing compositions are old in the art and any of these prior art compositions may be improved by the addition of monoperphthalic acid.

Illustrative of prior art effervescent denture composition is that shown in Table I of U.S. Pat. No. 4,405,486. Coloring agents and fragrances may also be included. Polytetrafluoroethylene is used as a pressing aid and binder as is the sodium perborate monohydrate which also is a bleaching agent. Anhydrous sodium perborate is used, primarily, as the agent to cause effervescence.

Similar compositions are taught in U.S. Pat. No. 2,931,776.

In the practice of this invention the monoperphthalic acid, which is preferably utilized as the magnesium salt, can be used as the sole oxygen source for bleaching. As such it is incorporated into a bicarbonate/organic acid composition to form an effervescent composition which is compressed into tablet form.

As used in the specification and claims the term monoperphthalate means monoperphthalic acid as well as salts thereof. While the acid form per se may be utilized, in the environment of the dental cleansing solution having a pH of about 6.5 or greater, the acid form will immediately be converted to the salt form. It will be appreciated by those skilled in the art that only the carboxylic acid moiety and not the peracid moiety is involved in the salt formation. The preferred salts are salts of divalent metals since two monoperphthalic acid groups are neutralized by a single metal atom resulting in a more active compound on a weight basis. The preferred salt is magnesium monoperphthalate.

In another embodiment of this invention the monoperphthalate may be used in conjunction with anhydrous sodium perborate resulting in an effervescent composition in which the perborate makes only a slight contribution to cleaning effectiveness.

In another embodiment of this invention the monoperphthalate can be utilized in conjunction with a monoperborate, percarbonate or monopersulfate. Alternatively, the perborate or percarbonate and monopersulfate can be utilized in the same composition.

Illustrative of the anhydrous perborate salts which may be used in the practice of this invention are sodium perborate, calcium perborate, ammonium perborate, magnesium perborate, and anhydrous potassium perborate. The anhydrous perborate is utilized at about 10 to about 20% by weight, preferably about 12 to about 18% by weight. Below 10% anhydrous perborate, the tablet will not disintegrate. There is no improved effectiveness above 20% by weight of anhydrous perborate.

The term "perborate" as used in the specification and claims includes any water soluble perborate salt either anhydrous or as the monohydrate. The term "persulfate" as used in the specification and claims means any water soluble monopersulfate as well as complex salts thereof. Illustrative of such monopersulfates are potassium monopersulfate and the complex salts thereof. Illustrative of the complex salts is a commercial product having the formula $KHSO_4 \cdot K_2HSO_4 \cdot 2KHSO_5$.

Where citric acid and sodium bicarbonate are utilized as the effervescent agent, they are used in approximately equimolar amounts. Sufficient sodium carbonate is used to adjust the pH of the solution of the denture cleansing agent in water to about 6.5 to 8.5.

A suitably sized tablet for cleaning dentures comprises about two to about ten grams. Where the sole oxygen liberating bleaching agent is monoperphthalic it comprises about 12% to about 70% by weight of the tablet, preferably about 15% to about 60% by weight, more preferably about 20 to about 45% by weight. Below about 12% of monoperphthalate, too large a tablet is required to effectively clean the denture. Above 70% the cost/benefit ratio is too large to justify using increased amounts of monoperphthalate. The denture cleansing composition of this invention will generally include sodium carbonate to adjust the pH of the cleansing solution to about 6.5 to about 11.0, preferably about 7.0 to about 9.0. A pH of below 8.5 is required where a citric acid/bicarbonate system is used since at higher pH, effervescence is diminished. A pH of about 7.0 to 8.0 is preferred. The bleaching agents are less effective at low pH. Hence, where anhydrous sodium perborate is the effervescent agent, a higher pH is preferred, e.g., 8.0 to 9.0. Above 11.0 the cleaning solution is so caustic as to become hazardous.

Sodium tripolyphosphate is used as a sequestering agent. Magnesium salts tend to cause cloudiness in the cleaning solution. Where the magnesium salt of monoperphthalic acid is used a sequestering agent is required to insure that the solution is clear. Additionally there may be other sources of magnesium such as impurities in other components of the composition. The use of sequestering agent is more for cosmetic purposes than improved effectiveness of the cleaning solution. Ethylene diaminetetracetic acid is also an effective sequestering agent. The term "sequestering agent" as used in the specification and claims means a compound capable of chelating metal ions to prevent precipitation thereof. However, when EDTA is used, the monoperphthalate must be compounded with other agents first in order to isolate it from the EDTA.

The sodium carbonate is used in an amount sufficient to adjust the pH to the desired range. Generally about 2% to about 40% by weight of the total composition is required, preferably about 3% to about 8% is required, more preferably about 4% to about 7% by weight. The sequestering agent is used at about 5% to about 30% by weight of the overall compositions. Preferably about 10 to about 20% by weight. As used in the specification and claims, unless otherwise stated, all weight percents are based on the overall composition.

Where a monopersulfate is incorporated into the composition the ratio of monopersulfate to monoperphthalate is about 8:1 to about 1:1; preferably about 6:1 to about 1:1 more preferably about 5:1 to about 4:1. The particular ratio used will depend on the cost/effectiveness parameters fixed for the desired composition. Although increasing levels of MPPA improve cleaning power, cost is increased proportionately.

The primary function of the anhydrous perborate is as an effervescent agent, to help disintegrate the tablet. Although it releases oxygen it does not appear to appreciably affect the cleansing power of the composition. Similarly, the monohydrate perborate does not contribute significantly to the cleaning power. Its primary function is as a binder or pressing aid. The term "pressing aid" as used in the specification and claims means a compound whose primary purpose is to assist in pressing and/or binding the composition together when it is tabletted or granulated.

Illustrative non-limiting examples of pressing aids useful in the practice of this invention are polymeric tetrafluorocarbons, e.g., polytetrafluoroethylene (teflon ®), polyvinyl pyrrolidone, perborate monohydrate salts heretofore described, and any waxy water soluble surfactants, e.g., ethoxylated alcohols, acids and phenols. It is customary in the art to use a minor amount of water, e.g., <1% by weight, to aid in the binding of the constituents during pressing. The pressing aid is utilized at about 0.1% to about 1.0% by weight preferably about 0.3% to about 0.8% by weight. The composition of this invention can be tabletted, granulated or used as a free flowing powder.

As used in the specification and claims the term "bleaching agent" includes the salts of monoperphthalic acid alone, the acid used in conjunction with an anhydrous perborate, a perborate monohydrate, a monopersulfate or mixtures thereof. As used in the specification and claims the term "effervescent agent" means the compound or compounds included in the denture cleaning composition to cause the composition, when immersed in water, to effervesce. Illustrative, non-limiting examples of such effervescent agents are anhydrous perborates and the combination of a water soluble bicarbonate with a solid water soluble acid. Illustrative non-limiting examples of bicarbonates useful in the practice of this invention are ammonium bicarbonate, potassium bicarbonate and sodium bicarbonate. Illustrative, non-limiting examples of solid, water soluble acids which may be used in conjunction with the bicarbonates are, citric acid, tartaric acid and succinic acid.

The organic acid and bicarbonate are utilized at approximately equimolar quantities. The amount of organic acid/bicarbonate mixture can vary from about 20% to about 40%, preferably about 22% to about 30%. If too small an amount is used the tablet will not disintegrate properly. Above 40% no appreciable benefit is seen in effectiveness of the composition and the tablet or granule may burst apart violently, causing splashing of the cleaning solution.

While the monoperphthalic acid is sufficiently stable alone to be utilized in the practice of this invention, its stability may be increased by compounding it with other compounds to be included in the composition, pressing it into tablets and granulating it for use in the denture cleansing composition of this invention. While the weight ratio of monoperphthalic acid to other compounding agents for the purpose of isolating the perphthalic acid is not critical, it is preferably about 5:1 to about 0.5:1 by weight, more preferably about 4:1 to about 1:1 most preferably about 3:1 to about 2:1 of monoperphthalic acid to other compounding agents.

By way of illustration the monoperphthalate may be compounded with sodium carbonate, sodium bicarbonate, citric acid and a minor amount of a polytetrafluorocarbon. The fluorocarbon is present in an amount of about 0.1% by weight to about 1.0% by weight based on the monoperphthalic acid plus other constituents. The sodium bicarbonate-citric acid combination is present at about 20% to about 40% by weight of the compounded composition.

In another embodiment the monoperphthalate can be blended with the solid water soluble acid and bicarbonate as well as the sodium carbonate and fluorocarbon. In that event the weight percent fluorocarbon is based on the monoperphthalic acid, bicarbonate and water soluble acid. In another embodiment the monoperphthalic acid is blended with about 1% to about 10% by weight of a water soluble surfactant such as ethoxylated phenol, an ethoxylated organic acid or an ethoxylated alcohol. The composition is granulated for use in the denture cleansing composition of this invention. Illustrative, non-limiting examples of the alcohol and organic acid moieties which may be used to form the water soluble surfactants are lauryl alcohol, lauric acid, palmitic acid, oleic acid, oleyl alcohol, decanol, decanoic acid, dodecyl alcohol, cyclohexanol and so forth. Pressing aids such as polyvinyl pyrrolidone an also be utilized at about 1 to about 5% by weight. Of course, combinations of different pressing aids can be used.

The advantages of the instant invention can be more readily appreciated by reference to the following examples. All percentages are by percent weight unless otherwise indicated.

EXAMPLE I

Various peroxides were tested to determine their stability by aging for four months at 23° C., 37° C. and 45° C. The active oxygen loss was measured for each condition. The results are shown in Table II.

TABLE II

Stability Studies of Selected Peroxides at Four Months

| Peroxygen Compound | Initial | Active Oxygen Percent by Weight | | |
| --- | --- | --- | --- | --- |
| | | Room Temperature | 37° C. | 45° C. |
| Oxone | (4.47 ± .01) % | 4.43 | 4.36 | 4.28 |
| Sodium Perborate Monohydrate | (14.6 ± 0.1) % | 14.6% | 14.7% | 14.7% |
| Phthalate[a] | (2.50 ± .03) % | 2.50 | 2.51 | 2.41[b] |
| Phthalate[a] + Sodium Carbonate | (1.84 ± .02) % | 1.71 | 1.49[c] | 1.23[d] |
| MCPABA[e] Sodium Sulfate | (1.49 ± .02) % | 1.29% (Loss 13%) | 0.91%[f] (Loss 39%) | 0.32%[g] (Loss 78%) |

[a]25% diperisophthalic acid in MgSO$_4$.
[b]Corrected for 5.0% weight loss (H$_2$O)
[c]Corrected for 1.7% weight loss (H$_2$O)
[d]Corrected for 3.9% weight loss (H$_2$O)
[e]Metachloroperbenzoic acid
[f]Corrected for 1.2% weight loss
[g]Corrected for 1.9% weight loss

EXAMPLE II

The stability of the magnesium salt of monoperphthalic acid (MPPA) was evaluated for various MPPA containing compositions at 55° C. for four days. This test is approximately the equivalent of three months at 23° C. The samples were packaged in foil and observed for puffing. Additionally, the active oxygen (A. O.) of the sample was determined. The results are shown in Table III. The compositions were blended and granulated prior to packaging.

TABLE III

Stability of Monoperphthalate

| | A | B | C | D |
| --- | --- | --- | --- | --- |
| Formulation | MPPA[a] | MPPA plus citric acid NaHCO$_3$ Na$_2$CO$_3$ | MPPA plus citric acid NaHCO$_3$ Na$_2$CO$_3$ ETDA etc.[b] | MPPA plus citric acid NaHCO$_3$ Na$_2$CO$_3$ Boric acid |
| Results | No A.O. loss No puffing | No A.O. loss No puffing | 32% loss in A.O.[c] No puffing | 77% loss in A.O. Puffing of package |

[a]Magnesium monoperphthalate.
[b]This composition also contained a detergent, a polytetrafluorocarbon, peppermint flavoring and sodium benzoate.
[c]Some or all of this loss is due to non-uniformity of granulation.

The results as shown in Table III demonstrate that MPPA alone or in granulations containing citric acid, sodium bicarbonate, and sodium carbonate are stable for at least three months. ETDA causes some instability of the MPPA when not previously isolated. Boric acid, on the other hand, causes severe decomposition of MPPA. EDTA is normally used as a sequestering agent for metals to insure that the cleansing solution is clear in appearance and to reduce the loss of active oxygen. With monoperphthalate, it is necessary to use another sequestering agent, e.g., sodium tripolyphosphate, unless the monoperphthalate is isolated from the EDTA.

EXAMPLE III

Various formulations of denture cleansing compositions were prepared and tested against a commercial denture cleansing agent. In order to test the compositions dental plaque was grown overnight on test tiles at 37° C. and stained with a mixture comprising equal volumes of coffee, tea, blueberry pie filling and grape juice. The tiles were left in contact with the stain mixture overnight (ca. 17 hrs.) at 23° C. The test results are shown in Table IV. The formulations were graded on a scale of 1 to 5 for cleaning effectiveness. A grade of 5 equals complete cleaning of the tile. The commercial product was graded at 1.5.

TABLE IV

Denture Cleansing Composition

| Ingredient | Runs Grams Per 100 Tablets | | | | |
|---|---|---|---|---|---|
| | A | B | C | D | E |
| MPPA[a] | 80.0 | 80.0 | 80.0 | 20.0 | — |
| Sodium Tripolyphosphate | 20.0 | 20.0 | 20.0 | 20.0 | 20.0 |
| Magnesium Stearate | 2.0 | 2.0 | 2.0 | 2.0 | 2.0 |
| Detergent | 2.0 | 2.0 | 2.0 | 2.0 | 2.0 |
| Polytetrafluoroethylene | 2.0 | 2.0 | 2.0 | 2.0 | 2.0 |
| Citric Acid | 30.0 | — | — | 30.0 | 30.0 |
| NaHCO$_3$ | 40.0 | — | — | 40.0 | 40.0 |
| Na$_2$CO$_3$ | 40.0 | — | — | 40.0 | 40.0 |
| Anhydrous Sodium Perborate | — | 70.0 | 70.0 | — | — |
| Sodium Perborate Monohydrate | — | — | 20.0 | 20.0 | 20.0 |
| Monopersulfate | — | — | — | 120.0 | 140.0 |
| Test Result | 3.0 | 3.0+ | 3.0+ | 3.5 | 1.5 |

[a]Monoperphthalic acid used as the magnesium salt.

As will be seen, not withstanding the fact that the anhydrous sodium perborate releases oxygen, it is primarily an effervescent agent and does not contribute to cleaning. While MPPA alone is an effective bleaching agent it is effective at lower levels when used in conjunction with monopersulfate. The compositions of Runs D and E show that there is a significant synergistic effect between MPPA and monopersulfate. All of the formulations of this invention, containing MPPA, are superior to the control.

The invention being thus described, it will be obvious that the same may be varied in many ways. Such variations are not to be regarded as a departure from the spirit of scope of the invention and all such modifications are intended to be included within the scope of the claims.

What is claimed is:

1. An effervescent denture cleansing composition, which comprises; an effervescent agent and a monoperphthalate as the bleaching agent in an amount of about 12% to about 70% by weight of the overall composition.

2. The composition according to claim 1 wherein the monoperphthalate is magnesium monoperphthalate.

3. The composition of claim 1 wherein the effervescent agent comprises an anhydrous perborate salt.

4. The composition of claim 3 wherein the anhydrous perborate salt is an anhydrous sodium perborate, calcium perborate, ammonium perborate, magnesium perborate and potassium perborate.

5. The composition according to claim 1 wherein a perborate monohydrate salt is incorporated into the composition as the effervescent agent.

6. The composition according to claim 5 wherein the perborate monohydrate is sodium perborate monohydrate.

7. The composition according to claim 1 wherein an additional bleaching agent comprising a water soluble monopersulfate salt is included in the composition.

8. The composition according to claim 7 wherein the monopersulfate salt is potassium monopersulfate.

9. The composition according to claim 1 wherein the effervescent agent comprises a water soluble organic acid and a water soluble bicarbonate.

10. The composition according to claim 9 wherein the water soluble organic acid is citric acid, tartaric acid or succinic acid.

11. The composition according to claim 9 wherein the bicarbonate is sodium bicarbonate, ammonium bicarbonate or potassium bicarbonate.

12. The composition according to claim 1 wherein sodium carbonate is present, in a amount sufficient so that a solution of the composition has a pH of about 6.5 to 11.0.

13. The composition according to claim 12 wherein the amount of sodium carbonate is sufficient so that the solution pH is about 7.0 to about 9.0.

14. The composition according to claim 1 wherein a sequestering agent is included.

15. The composition according to claim 14 wherein the sequestering agent is sodium tripolyphosphate or ethylenediamene tetracetic acid.

16. The composition according to claim 1 wherein the monoperphthalate is present at about 20% to about 45% by weight of the overall composition.

17. The composition according to claim 7 wherein the weight ratio of monopersulfate to monoperphthalate is about 8:1 to about 1:1.

18. The composition according to claim 17 wherein the weight ratio of monopersulfate to monoperphthalate is about 6:1 to about 1:1.

19. The composition according to claim 1 wherein the sequestering agent is sodium tripolyphosphate utilized at about 5% to about 30% by weight of the overall composition.

20. The composition according to claim 1 wherein the bleaching agent is a mixture of magnesium monoperphthalate and a potassium monpersulfate.

21. The composition according to claim 20 wherein the magnesium monoperphthalate is present at about 15% to about 60% by weight based on the overall composition and the weight ratio of monopersulfate to magnesium monoperphthalate is about 6:1 to about 1:1.

22. The composition according to claim 1 wherein the effervescent agent is an anhydrous perborate salt or a mixture of a water soluble organic acid and a water soluble bicarbonate salt.

23. The composition according to claim 22 wherein the anhydrous perborate is an anhydrous sodium perborate, ammonium perborate, potassium perborate, calcium perborate and magnesium perborate and is included in the composition at about 10% to about 20% by weight based on the overall composition.

24. The composition according to claim 22 wherein the effervescent agent is a mixture of an organic acid and a bicarbonate salt wherein the organic acid is citric acid, succinic acid or tartaric acid and the bicarbonate salt is sodium bicarbonate, ammonium bicarbonate or potassium bicarbonate.

25. The composition according to claim 24 wherein the organic acid and bicarbonate are present in substantially equimolar quantities and the mixture is present in the composition at about 22% to about 30% by weight.

26. The composition according to claim 1 wherein the sodium carbonate is included in the composition at about 2% to about 10% and is present in an effective amount so that a solution of the composition exhibits a pH of about 6.0 to about 11.0.

27. The composition according to claim 26 wherein the effervescent agent is an anhydrous perborate salt and the sodium carbonate is present in amount sufficient to adjust the pH of a solution of the composition to about 6.5 to 11.0.

28. The composition according to claim 1 wherein the pressing aid is a polymeric tetrafluorocarbon, polyvinyl pyrrolidone, a water soluble ethoxylated alcohol, a water soluble ethoxylated phenol, a water soluble ethoxylated organic acid or mixtures thereof.

29. The composition according to claim 28 wherein the pressing aid is included in the composition at about 0.3% to about 0.8% by weight based on the overall composition.

30. A denture cleansing composition, which comprises;
(a) About 12% to about 70% by weight of a monoperphthalate as the bleaching agent;
(b) about 5% to about 30% by weight of a sequestering agent;
(c) about 0.1% to about 1.0% by weight of a pressing aid;
(d) about 2% to about 40% by weight of sodium carbonate, and
(e) remainder being an effervescent agent.

31. The composition according to claim 30 wherein the bleaching agent is a mixture of monoperphthalate and potassium monopersulphate, wherein the weight ratio of monopersulfate to monoperphthalate is about 8:1 to about 1:1.

* * * * *

UNITED STATES PATENT AND TRADEMARK OFFICE
CERTIFICATE OF CORRECTION

PATENT NO. : 4,490,269
DATED : December 25, 1984
INVENTOR(S) : Andrew R. Gallopo It is certified that error appears in the above-identified patent and that said Letters Patent are hereby corrected as shown below:

In claims 19, 20, 22, 26 and 28 at line 1 of each claim please change the dependency from "claim 1" to --claim 30--.

Signed and Sealed this

Fourteenth Day of May 1985

[SEAL]

Attest:

DONALD J. QUIGG

Attesting Officer  Acting Commissioner of Patents and Trademarks